United States Patent [19]

Parker et al.

[11] Patent Number: 5,077,315
[45] Date of Patent: Dec. 31, 1991

[54] ARYLOXY ALKANOLS AS ANTI-RETROVIRUS AGENTS

[75] Inventors: Roger A. Parker; Sai P. Sunkara, both of Cincinnati, Ohio

[73] Assignee: Merrell Dow Pharmaceuticals, Cincinnati, Ohio

[21] Appl. No.: 541,868

[22] Filed: Jun. 21, 1990

Related U.S. Application Data

[62] Division of Ser. No. 284,146, Dec. 14, 1988, Pat. No. 4,939,173.

[51] Int. Cl.$^5$ .................. A61K 31/075; A61K 31/22
[52] U.S. Cl. .................. 514/718; 514/546; 514/549
[58] Field of Search .................. 514/718, 546, 549

Primary Examiner—Jerome D. Goldberg
Attorney, Agent, or Firm—Edlyn S. Simmons

[57] ABSTRACT

Aryloxyalkanol derivatives having the formula

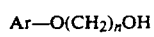

wherein n is an integer from 3 to 8 and Ar is (1) 1- or 2-naphthylenyl, (2) phenyl optionally substituted by from 1 to 3 $C_{1-4}$ lower alkyl groups, or (3) a diphenyl moiety of structure

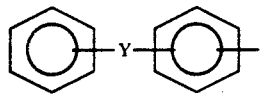

wherein Y is a bond, $CH_2$ or $CH_2O$, and esters thereof have antiretrovirus activity and are effective in a method for treatment of a retrovirus infection.

7 Claims, No Drawings

ARYLOXY ALKANOLS AS ANTI-RETROVIRUS AGENTS

CROSS-REFERENCE TO RELATED APPLICATIONS

This is a divisional of application Ser. No. 284,146, filed Dec. 14, 1988, U.S. Pat. No. 4,939,173, July 3, 1990.

FIELD OF INVENTION

The present invention relates to the use of certain aryloxyalkanols and esters thereof with pharmaceutically acceptable acids in the treatment of retroviral infections including HIV infections.

BACKGROUND OF THE INVENTION

A great deal of research is currently underway to develop treatments and cures for viral infections in humans and in animals. Notably the incidence of acquired immune deficiency syndrome (AIDS) and AIDS related complex (ARC) in humans is increasing at an alarming rate. The five year survival rate for those with AIDS is dispiriting and AIDS patients, whose immune systems have been seriously impaired by the infection, suffer from numerous opportunistic infections including Kaposi's sarcoma and *Pneumocystis carninii* pneumonia. No cure is known and current treatments are largely without adequate proof of efficacy and have numerous untoward side effects. Fear of the disease has resulted in social ostracism of and discrimination against those having or suspected of having the disease.

Retroviruses are a class of ribonucleic acid (RNA) viruses that replicate by using reverse transcriptase to form a strand of complementary DNA (cDNA) from which a double stranded, proviral DNA is produced. This proviral DNA is then randomly incorporated into the chromosomal DNA of the host cell. Further transcription and translation of the integrated viral genome DNA results in viral replication through the synthesis of virus specific RNA and proteins.

Many of the known retroviruses are oncogenic or tumor causing. Indeed the first two human retroviruses discovered, denoted human T-cell leukemia virus I and II or HTLV-I and II, were found to cause rare leukemias in humans after infection of T-lymphocytes. The third such human virus to be discovered, HTLV-III, now referred to as HIV, was found to cause cell death after infection of T-lymphocytes and has been identified as the causative agent of acquired immune deficiency syndrome (AIDS) and AIDS related complex (ARC).

Among the substances previously shown to have activity against HIV and other retroviruses are such diverse compounds as azidothymidine, castanospermine, and heparin.

The applicants have now discovered that certain aryloxyalkanols, more specifically certain naphthylenyl, biphenylyl, benzylphenyl, benzyloxyphenyl, and substituted and unsubstituted phenyl ethers of $C_{3-8}$ straight-chain α,ω-glycols, esters thereof with pharmaceutically acceptable acids, and the salts thereof, are useful in the treatment of various retroviral infections including in the treatment of AIDS and ARC resulting from infection by HIV or other retroviruses.

SUMMARY OF THE INVENTION

The anti-retrovirus aryloxyalkanols of this invention have the general Formula I

wherein n is an integer from 3 to 8 and Ar is (1) 1- or 2-naphthylenyl, (2) phenyl optionally substituted by from 1 to 3 $C_{1-4}$ lower alkyl groups, or (3) a diphenyl moiety of structure

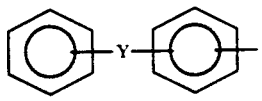

wherein Y is a bond, $CH_2$ or $CH_2O$.

The use as anti-retroviral agents of esters of compounds of Formula I with pharmaceutically acceptable acids and salts of said esters is also included within the scope of this invention.

Many compounds of Formula I are known in the prior art, and the use of some of these compounds for treatment and prophylaxis of infection has been described in British patent 2,068,952, but their usefulness in treatment of diseases caused by infection with a retrovirus has not hitherto been known.

DETAILED DESCRIPTION OF THE INVENTION

When Ar represents naphthylenyl, the hydroxyalkoxy group may be in the 1- or 2- position of the naphthylene moiety. When Ar represents substituted phenyl, the substituents are straight- or branched-chain alkyl group having from 1 to 4 carbon atoms. The alkyl groups are exemplified by methyl, ethyl, propyl, isopropyl, n-butyl, isobutyl, sec-butyl and tert-butyl. The preferred alkyl substituent is methyl. The alkyl substituents may be in the ortho, meta or para positions relative to the hydroxyalkoxy chain and, when 2 or 3 alkyl groups are present, to one another.

In the compounds of Formula I wherein Ar represents, a diphenyl moiety of structure

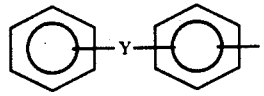

substituent Y may be disposed ortho, meta or para to the hydroxyalkoxy chain on the benzene ring common to both, preferably meta or para, and most preferably in the para orientation.

The linear, saturated carbon chain linking the ether with the hydroxyl group may range in length from 3 to 8 carbon atoms. Compounds having a chain length of 6 methylene units are preferred.

Esters of the compounds of Formula I with pharmaceutically acceptable acids also show anti-retrovirus activity. The alcohols are often difficulty soluble in water. Esterification with a solubilizing pharmaceutically acceptable acid, preferably a polycarboxylic acid, increases water solubility and facilitates absorption of the compound. Particularly desirable esters include monoesters of polycarboxylic acids and/or the salts of such monoesters, preferably sodium salts.

Suitable esters include esters of alkanoic, alkenoic, alkenedioic and alkanedioic acids having from 1 to 4 carbon atoms, for example, acetic, butyric, malonic, maleic, succinic, and fumaric acids. Esters of these acids and the alkanols of Formula I are prepared by methods well known to the art. For example, maleates and succinates are conveniently prepared by reacting the compound with maleic or succinic anhydride in pyridine, followed by acidification and isolation of the monoester.

Illustrative compounds of this invention are:
6-phenoxyhexan-1-ol,
6-(2,4,6-trimethylphenoxy)hexan-1-ol,
6-(4-phenylphenoxy)hexan-1-ol,
6-(4-benzylphenoxy)hexan-1-ol,
6-(4-benzyloxyphenoxy)hexan-1-ol
6-(2-naphthylenyloxy)hexan-1-ol.

Also included are compounds analogous to each of the foregoing having another unbranched alkylene chain of from 3 to 8 carbon atoms in place of the hexamethylene chain, e.g., 3-(4-phenylphenoxy)propan-1-ol through 8-(4-phenylphenoxy) octan-1-ol, and the corresponding alcohols in each series above.

Included also are isomers of each of the foregoing compounds having the hydroxyalkoxy group and Y meta or ortho to one another on the central benzene ring common to both, e.g., 6-(3-benzyloxyphenoxy)hexan-1-ol, 6-(2-phenylphenoxy)-hexan-1-ol, and the corresponding ortho and meta isomers of each of the compounds hereinabove.

Also included are pharmaceutically acceptable esters of each of the above alcohols with various acids, more specifically, monoesters with maleic, succinic, fumaric, and acetic acids.

The ability of the aryloxyalkanol derivatives of this invention to act as anti-retroviral agents can be demonstrated by their ability to inhibit the growth and replication of murine leukemia virus, an oncogenic retrovirus, as determined by an in vitro XC plaque assay. This assay was performed according to the method of Rowe et al. (*Virology*, 1970, 42, 1136–39) as previously described by L. Hsu, et al. (*J. Virological Methods*, 1980, 1, 167–77) and T. L. Bowlin and M. R. Proffitt (*J. Interferon Res.*, 1983, 3(1), 19–31). Mouse SC-1 cells (fibroblast) ($10^5$) were seeded into each well of 6-well cluster plates (Costar #3506) in 4 ml Minimum Essential Medium (MEM) with 10% Fetal Calf Serum (FCS). Following an 18 hour incubation period (37° C.), Moloney murine leukemia virus (MoLV) was applied at a predetermined titer to give optimal (i.e. countable) numbers of virus plaques. Compounds were added 2 hours prior to addition of the virus. Three days later the culture medium was removed, the SC-1 cell monolayers were exposed to UV irradiation (1800 ergs), and rat XC cells ($10^6$) were seeded into each well in 4 ml MEM. Following an additional 3 day incubation (37° C.), these cells were fixed with ethyl alcohol (95%) and stained with 0.3% crystal violet. Plaques were then counted under low magnification. The antiviral activities of various compounds of this invention are tabulated in Table I in terms of the $IC_{50}$, i,e, the concentration giving a 50% inhibition of virus plaque growth.

TABLE 1
INHIBITORY CONCENTRATION OF VARIOUS
ARYLOXYALKANOL DERIVATIVES OF FORMULA I
AGAINST MURINE LEUKEMIA VIRUS

| Compound | Ar | n | IC50 ($\mu$g/ml) |
| --- | --- | --- | --- |
| 6-Phenoxyhexan-1-ol | Phenyl | 6 | 1 |
| 6-(2,4,6-Trimethylphenoxy)hexan-1-ol | 2,4,6-Trimethylphenyl | 6 | 5 |
| 6-(4-Phenylphenoxy)hexan-1-ol | 4-Phenylphenyl | 6 | 2.5–5 |
| 6-(4-Phenylphenoxy)hexyl succinate monoester | 4-Phenylphenyl | 6 | 1–10 |
| 6-(4-Benzylphenoxy)hexan-1-ol | 4-Benzylphenyl | 6 | 1–10 |
| 4-(4-Benzyloxyphenoxy)butan-1-ol | 4-Benzyloxyphenyl | 4 | 1–10 |
| 6-(4-Benzyloxyphenoxy)hexan-1-ol | 4-Benzyloxyphenyl | 6 | 1–10 |
| 6-(2-Naphthylenyloxy)hexan-1-ol | 2-Naphthylenyl | 6 | 5–10 |

To further confirm the antiretroviral activity of these compounds, 6-(4-phenylphenoxy)hexan-1-ol was evaluated for activity against HIV. Following overnight pretreatment of T-cells (JM cells) with the HIV1GB8 strain of HIV-1, 6-(4-phenylphenoxy)hexan-1-ol was added to the cell cultures at concentrations of 15 and 7.5 $\mu$g/ml. After 4 days the the number of synctial cells in the cell culture and the amount of p24 antigen, also a measure of viral replication, were determined. The data are shown in Table 2.

TABLE 2
ANTI-HIV ACTIVITY OF
6-(4-PHENYLPHENOXY)HEXAN-1-OL

| TREATMENT | SYNCYTIAL COUNT | % INHIBITION | P24 ANTIGEN pg $\times$ $10^3$/ml |
| --- | --- | --- | --- |
| Untreated | 29 | — | 801 |
| 6-(4-Phenylphenoxy)hexan-1-ol, 15 $\mu$g/ml | 0 | 100 | 62 |
| 6-(4-Phenylphenoxy)hexan-1-ol, 7.5 $\mu$g/ml | 8 | 72 | Not determined |

The aryloxyalkanol derivatives of this invention can be used to treat a number of diseases and conditions known to be caused by retroviruses including those diseases and conditions caused by murine leukemia virus, feline leukemia virus, avian sarcoma virus, human immunodeficiency virus (HIV), HTLV-I, and HTLV-II. Those experienced in this field are readily aware of the circumstances requiring anti-retroviral therapy. Applicants consider the use of the aryloxyalkanol derivatives of this invention to treat HIV infections in humans to be of most importance. The term "patient" used herein is taken to mean mammals such as primates, including humans, sheep, horses, cattle, pigs, dogs, cats, rats and mice, and birds.

The amount of the aryloxyalkanol derivative of formula I to be administered can vary widely according to the particular dosage unit employed, the period of treatment, the age and sex of the patient treated, the nature and extent of the disorder treated, and the particular aryloxyalkanol derivative selected. Moreover the aryloxyalkanol derivative can be used in conjunction with other agents known to be useful in the treatment of retroviral diseases and agents known to be useful to treat the symptoms of and complications associated with diseases and conditions caused by retroviruses. The antiretrovirally effective amount of an aryloxyalkanol derivative of formula I to be administered will generally range from about 15 mg/kg to 500 mg/kg. A unit dosage may contain from 25 to 500 mg of the aryloxyalkanol derivative, and can be taken one or more times per day. The aryloxyalkanol derivative can be administered with a pharmaceutical carrier using conventional dosage unit forms either orally or parenterally.

The preferred route of administration is oral administration. For oral administration the aryloxyalkanol derivative can be formulated into solid or liquid preparations such as capsules, pills, tablets, troches, lozenges, melts, powders, solutions, suspensions or emulsions. The solid unit dosage forms can be capsules, which can be of the ordinary hard- or soft-shelled gelatin type containing, for example, surfactants, lubricants, and inert fillers such as lactose, sucrose, calcium phosphate and cornstarch. In another embodiment the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration, such as potato starch, alginic acid, corn starch and guar gum, lubricants intended to improve the flow of tablet granulations and to prevent the adhesion of tablet material to the surfaces of the tablet dies and punches, for example, talc, stearic acid, or magnesium, calcium or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The aryloxyalkanol derivatives of this invention may also be administered parenterally, that is, subcutaneously, intravenously, intramuscularly or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol or hexadecyl alcohol, glycols such as propylene glycol or polyethylene glycol, glycerol ketals such as 2,2-dimethyl1,3-dioxolane-4-methanol, ethers such as poly(ethylene glycol) 400, an oil, a fatty acid, a fatty acid ester or glyceride, or an acetylated fatty acid glyceride, with or without the addition of a pharmaceutically acceptable surfactant such as a soap or a detergent, a suspending agent such as pectin, carbomers, methylcellulose, hydroxypropylmethylcellulose or carboxymethylcellulose, or an emulsifying agent, and other pharmaceutical adjuvants. Illustrative of oils which can be used in the parenteral formulations of this invention are those of petroleum, animal, vegetable, and synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl β-aminopropionates and 2-alkylimidazoline quarternary ammonium salts, as well as mixtures. The parenteral compositions of this invention will typically contain from about 0.5 to about 25% by weight of the aryloxyalkanol derivative of formula I in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The compounds of Formula I are generally prepared by Williamson ether synthesis (J. March, "Advanced Organic Chemistry—Reactions, Mechanisms and Structure," McGraw-Hill Book Company, New York, 1968, p. 316). The reaction is illustrated in the following reaction scheme:

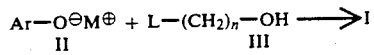

$$\text{Ar}-\text{O}^{\ominus}\text{M}^{\oplus} + \text{L}-(\text{CH}_2)_n-\text{OH} \longrightarrow \text{I}$$
$$\quad\text{II} \qquad\qquad\qquad \text{III}$$

In the above reaction sequence, L represents a halogen atom, such as chlorine, bromine or iodine, or a sulfonate ester such as methanesulfonate or p-toluenesulfonate; M+ represents a metal ion such as lithium, sodium, potassium, silver or mercury; and Ar and n are as defined for Formula I.

A phenoxide or naphthoxide salt, represented by structure II and conveniently formed in situ by addition of a base such as sodium methoxide, potassium carbonate, sodium hydride or potassium hydroxide to the corresponding phenol or naphthol, is reacted with an alcohol bearing a leaving group on the terminal carbon atom, and having the structure III. The leaving group is displaced, resulting in the formation of a carbon-oxygen ether bond.

The starting naphthols and phenols which are the precursors of the naphthoxide and phenoxide salts are generally commercially available or are available by entirely conventional synthetic methods well-known in the art. For example, benzyloxyphenols can be prepared by reaction of benzyl halides with hydroquinones or resorcinols, or with their monoesters, with subsequent hydrolysis.

The benzylphenols are readily prepared by reduction of the corresponding hydroxybenzophenones. The latter are prepared, for example, by Friedel-Crafts benzoylation of phenyl acetate, by Fries rearrangement of phenyl benzoates, or by oxidation of benzhydryl alcohols.

Phenylphenol may be prepared by the Ullmann reaction of a phenoxide and a halophenyl ester, in the presence of copper salts. See March, "Advanced Organic Chemistry," pages 500-508 (McGraw-Hill, New York, 1968).

The ω-substituted linear alcohols, III, used in the sequence are also generally available commercially or by well-known, conventional synthetic methods. For example, the α,ω-diol may be converted to the -haloalcohol using triphenylphosphine and carbon tetrahalide (see C.A., 63, 13137c (1965) for the preparation of 12-bromododecane-1-ol).

The Williamson reaction may be carried out with or without solvents. Suitable solvents for the reaction incude lower alcohols, such as ethanol and isopropanol, ketones such as acetone and butanone, or amides such as dimethylformamide and dimethylacetamide. Other suitable solvents include dimethylsulfoxide, acetonitrile, dimethoxyethane, tetrahydrofuran and toluene.

The temperature of the reaction may vary from about 0° C. to the reflux temperature of the solvent, and the reaction time may vary from about 0.5 hour to 80 hours.

The reaction is conveniently worked up by extraction of the product into an organic solvent such as ether, dichloromethane, chloroform, toluene or the like, washing with brine, drying over sodium or magnesium sulfate, and evaporation of the solvent. Purification is generally effected by distillation or crystallization from a suitable solvent.

Esters of compounds of Formula I are formed by conventional methods, such as reaction of the alcohol of Formula I with an acid, an acid halide, an anhydride, or other activated acyl derivative, often in the presence of an acid acceptor. The product is isolated in a conventional fashion and purified by distillation or crystallization from an appropriate solvent. Salts of monesters of polybasic acids are prepared by addition of base, e.g., NaH, to an ether solution of the ester, followed by filtration of the resultant precipitate.

EXAMPLE 1 6-(4-Phenylphenoxy)hexan-1-ol

A mixture of 34.0 g (0.2 mole) or p-phenylphenol (Eastman) and 10.8 g (0.2 mole) of sodium methoxide (MCB) in 500 ml of dry dimethylformamide is heated and stirred on a steam bath for 0.5 hour, after which 27.3 g (0.2 mole) of 6-chlorohexan-1-ol (MCB) and about 2 g of sodium iodide are added. The mixture is heated to reflux with stirring, and then allowed to cool to room temperature. The reaction mixture is partitioned between ether/acetone and water, and the organic phase is extracted with base, washed with water and brine, dried ($Na_2SO_4$), and the solvent evaporated. The resultant white solid product is recrystallized twice from methanol/acetone, to give the desired product, m.p. 103°-105° C.

EXAMPLE 2 6-(4-Benzyloxyphenoxy)hexan-1-ol

A mixture of 106.0 g (0.53 mole) of p-benzyloxyphenol (Eastman), 28.6 g (0.53 mole) sodium methoxide (MCB) and about 2 g of sodium iodide in 600 ml of dimethylformamide is stirred for 5 minutes, after which 73 g (0.53 mole) of 6-chlorohexan-1-ol (MCB) is added, and the mixture is refluxed with stirring. The methanol formed in the reaction is allowed to distill off. After 2 hours reflux, the mixture is diluted with ice and water, 500 ml of 10% potassium hydroxide is added, and the resultant precipitate collected and dried. The solid is combined with 1 liter of butanone, refluxed and filtered. The residue is cooled, whereupon the desired product crystallizes out. The solid product is stirred with 1 liter of acetone at room temperature, the mixture is filtered to separate additional insoluble byproduct, the acetone boiled off and replaced with methanol, and the methanolic solution cooled to crystallize out the desired product, m.p. 94°-97° C.

EXAMPLE 3 6-(4-Benzylphenoxy)hexan-1-ol

A mixture of 40.0 g (0.217 mole) of p-benzylphenol (Eastman) and 29.7 g (0.217 mole) of 6-chlorohexan-1-ol (MCB) in 500 ml of dry dimethylformamide is stirred and heated to about 100° C., after which 33.1 g (0.24 mole) of potassium carbonate is added, and the mixture refluxed for 2.5 hours. The mixture is cooled, poured into ice-water, and 50 ml of 10% NaOH is added. The mixture is extracted with ether, the ether extracts washed with water and brine, dried ($MgSO_4$), and the ether evaporated. The resultant oil is redistilled to give the product as a water-white oil fraction distilling at 140°-175° C., 0.05 mmHg.

EXAMPLE 4 6-(3-Phenylphenoxy)hexan-1-ol

A mixture of 15.0 g (0.088 mole) of 3-hydroxybiphenyl, 13.3 g (0.097 mole) of 6-chlorohexan-1-ol, and 13.8 g (0.01 mole) of potassium carbonate in 250 ml of dry dimethylformamide is stirred and heated to reflux for 3 hours. The mixture is cooled to room temperature, diluted with water, and extracted with ether, the ether extracts dried and evaported under reduced pressure to give a light yellow oil. The crude product is vacuum distilled to give a fraction boiling between 150° and 190° C. (0.05 mmHg), and solidifying to a soft solid, corresponding to the pure desired product.

EXAMPLE 5

Using the procedure of Example 2, the following phenolic compounds may be reacted with the indicated haloalcohols to produce the compounds shown below (Ph=phenyl):

| Phenol | Haloalcohol | Product | M.P. (°C.) |
| --- | --- | --- | --- |
| p-Ph—Ph—OH | 4-Cl—$(CH_2)_4$—OH | p-Ph—Ph—O—$(CH_2)_4$—OH | 110-113° |
| p-Ph—Ph—OH | 5-Cl—$(CH_2)_5$—OH | p-Ph—Ph—O—$(CH_2)_5$—OH | 108-109° |
| p-Ph—Ph—OH | 8-Cl—$(CH_2)_8$—OH | p-Ph—Ph—O—$(CH_2)_8$—OH | 103-106° |
| p-(Ph—$CH_2$—O)—Ph—OH | 4-Cl—$(CH_2)_4$—OH | p-(Ph—$CH_2$—O)—Ph—O—$(CH_2)_4$—OH | 97-99° |
| p-(Ph—$CH_2$—O)—Ph—OH | 5-Cl—$(CH_2)_5$—OH | p-(Ph—$CH_2$—O)—Ph—O—$(CH_2)_5$—OH | 90-93° |

EXAMPLE 6

6-[4-Phenylphenoxy)-1-hexyl succinate (monoester)

A mixture of 10 g (0.037 mole) of 6-(4-phenylphenoxy) hexan-1-ol, prepared in Example 1, and 10 g of succinic anhydride in 250 ml of pyridine is refluxed with stirring for 3 hours. The pyridine is removed under vacuum on a steam bath, the residue poured into water and acidified with HCl. The resultant precipitate is collected, washed, dried and recrystallized from butanone, to give the pure monoester, m.p. 113°–115° C.

EXAMPLE 7

Solution

| Solution | |
|---|---|
| 6-(4-Phenylphenoxy)hexan-1-ol | 0.85 g |
| Alcohol | 78.9 ml |
| Isopropyl Myristate | 5.0 g |
| Polyethylene Glycol 400 (Av. M.W. 400) | 10.0 g |
| Purified Water sufficient to make | 100 ml |

Combine the alcohol, isopropyl myristate and polyethylene glycol 400 and dissolve the drug substance therein. Add sufficient purified water to give 100 ml.

EXAMPLE 8

| Tablet | |
|---|---|
|  | For 15,000 |
| 6-(4-Benzyloxyphenoxy)hexan-1-ol | 75 g |
| Lactose | 1.216 kg |
| Corn Starch | 0.3 kg |

Mix the active ingredient, the lactose and corn starch uniformly. Granulate with 10% starch paste. Dry to a moisture content of about 2.5%. Screen through a No. 12 mesh screen. Add and mix the following:

| Magnesium | 0.015 kg |
|---|---|
| Corn Starch sufficient to make | 1.725 kg |

Compress on a suitable tablet machine to a weight of 0.115 g/tablet.

EXAMPLE 9 Soft Gelatin Capsule

| Soft Gelatin Capsule | |
|---|---|
| 6-(4-Phenylphenoxy)hexan-1-ol | 0.25 kg |
| Polysorbate 80 (Polyoxyethylene (20) sorbitan mono-oleate) | 0.25 kg |
| Corn Oil sufficient to make | 25.0 kg |

Mix and fill into 50,000 soft gelatin capsules.

What is claimed is:

1. A method of treating a retroviral infection in a patient in need thereof which comprises administering to said patient an anti-retrovirally effective amount of a compound of the formula:

$$Ar-O(CH_2)_nOH$$

wherein n is an integer from 3 to 8 and Ar is phenyl or phenyl substituted by from 1 to 3 $C_{1-4}$ lower alkyl groups, an ester thereof with a $C_{1-4}$ alkanoic, alkenoic, alkanedioic or alkenedioic acid having from 1 to 4 carbon atoms, or a pharmaceutically acceptable salt thereof.

2. A method according to claim 1 wherein n is 6.

3. A method according to claim 1 wherein AR is phenyl.

4. A method according to claim 1 wherein the compound is 6-phenoxyhexan-1-ol, an ester thereof with a $C_{1-4}$ alkanoic, alkenoic, alkanedioic or alkenedioic acid having from 1 to 4 carbon atoms, or a pharmaceutically acceptable salt thereof.

5. A method according to claim 4 wherein the compound is 6-phenoxyhexan-1-ol.

6. A method according to claim 1 wherein the compound is 6-(2,4,6-trimethylphenoxy)hexan-1-ol, an ester thereof with a $C_{1-4}$ alkanoic, alkenoic, alkanedioic or alkenedioic acid having from 1 to 4 carbon atoms, or a pharmaceutically acceptable salt thereof.

7. A method according to claim 6 wherein the compound is 6-(2,4,6-trimethylphenoxy)hexan-1-ol.

* * * * *